(12) United States Patent
Cervenka et al.

(10) Patent No.: US 9,938,233 B2
(45) Date of Patent: Apr. 10, 2018

(54) PURIFICATION OF X-RAY CONTRAST AGENTS

(71) Applicant: GE Healthcare AS, Oslo (NO)

(72) Inventors: Jan Cervenka, Oslo (NO); Mikkel Thaning, Oslo (NO); Andreas Olsson, Oslo (NO); Christian Glogard, Oslo (NO)

(73) Assignee: GE Healthcare AS, Oslo (NO)

( * ) Notice: Subject to any disclaimer, the term of this patent is extended or adjusted under 35 U.S.C. 154(b) by 228 days.

(21) Appl. No.: 14/442,203

(22) PCT Filed: Nov. 19, 2013

(86) PCT No.: PCT/US2013/070699
§ 371 (c)(1),
(2) Date: May 12, 2015

(87) PCT Pub. No.: WO2014/099214
PCT Pub. Date: Jun. 26, 2014

(65) Prior Publication Data
US 2016/0304440 A1    Oct. 20, 2016

(30) Foreign Application Priority Data
Dec. 19, 2012 (EP) .................................... 12198020

(51) Int. Cl.
*A61K 49/04* (2006.01)
*C07C 231/24* (2006.01)
*C07C 237/46* (2006.01)

(52) U.S. Cl.
CPC ........ *C07C 231/24* (2013.01); *A61K 49/0438* (2013.01); *C07C 237/46* (2013.01); *A61K 49/0447* (2013.01)

(58) Field of Classification Search
None
See application file for complete search history.

(56) References Cited

U.S. PATENT DOCUMENTS

| | | | |
|---|---|---|---|
| 5,221,485 A | 6/1993 | Bosworth et al. | |
| 5,447,635 A | 9/1995 | Viscardi et al. | |
| 5,447,653 A | 9/1995 | Yanagita et al. | |
| 5,811,581 A | 9/1998 | Piva et al. | |
| 9,474,808 B2 | 10/2016 | Birkeland | |
| 2001/0021828 A1 | 9/2001 | Fischer et al. | |
| 2010/0322868 A1 | 12/2010 | Thaning | |
| 2011/0021823 A1 | 1/2011 | Homestad et al. | |

FOREIGN PATENT DOCUMENTS

| | | |
|---|---|---|
| CN | 101687051 A | 3/2010 |
| CN | 101962330 A | 2/2011 |
| EP | 0575360 B1 | 8/1994 |
| EP | 0902686 B1 | 11/1999 |
| EP | 2281623 A1 | 2/2011 |
| EP | 2655318 A1 | 10/2013 |
| EP | 2935204 A1 | 10/2015 |
| JP | 6-506142 A | 7/1994 |
| JP | 2000-504735 A | 4/2000 |
| JP | 2014-511344 A | 5/2014 |
| RU | 2135462 C1 | 8/1999 |
| WO | 1992/014539 A1 | 9/1992 |
| WO | 97/30735 A2 | 8/1997 |
| WO | 2006/016815 A1 | 2/2006 |
| WO | 2007/013816 A1 | 2/2007 |
| WO | 2007064220 A1 | 6/2007 |
| WO | 2009/008734 A2 | 1/2009 |
| WO | 2009/091758 A1 | 7/2009 |
| WO | 2011/063551 A1 | 6/2011 |
| WO | 2012/084926 A1 | 6/2012 |
| WO | 2014/099214 A1 | 6/2014 |

OTHER PUBLICATIONS

Wistrand et al., "GE-145, a new low-osmolar dimeric radiographic contrast medium", ACTA Radiologica, Stockholm, Sweden, 1987, Nov. 2010, vol. 51, No. 9, pp. 1014-1020.
Supplemental European Search Report regarding EP Application No. 13864437, dated Jul. 19, 2016, 12 pages.
Search Report and Written Opinion regarding SG Application No. 11201504201R, dated Jun. 22, 2016, 9 pages.
International Search Report and Written Opinion regarding International Application No. PCT/US2013/070699, dated Mar. 10, 2014, 8 pages.
GE Healthcare, Visiplaque (iodixanol) injection' [data sheet], Nov. 2010 [retrieved on Feb. 14, 2014]. Retrieved from the Internet <URL: http://www3.gehealthcare.com/~/media/Downloads/us/Product/Product-Categories/Contrast-Media_Non-Gatekeeper/Visipaque/GEHealthcare-Visipaque-PrescribingInfo-20101101.pdf>; p. 1, left column, section 'description'.
Chinese Search Report regarding Chinese Application No. 201380066485.8, dated Apr. 15, 2016, 2 pages.
International Preliminary Report on Patentability Received for PCT Application No. PCT/US2013/070699 dated Jun. 23, 2015, 5 Pages.
Office Action Recieved for Japanese Patent Application No. 2015-549398, dated Mar. 28, 2017, 5 Pages.
Chai et al., "Predicting Cardiotoxicity Propensity of the Novel Iodinated Contrast Medium GE-145: Ventricular Fibrillation During Left Coronary Arteriography in Pigs", Acta Radiologica, vol. 51, No. 9, 2010, pp. 1007-1013.
Office Action Received for European Patent Application No. 13864437.2, dated Oct. 2, 2017, 7 Pages.
Office Action+ Search Report Received for Russian Patent Application No. 2015121502/04, dated Sep. 27, 2017, 12 Pages (6 Pages of English Translation + 6 Pages Official Copy).

*Primary Examiner* — Michael G Hartley
*Assistant Examiner* — Melissa J Perreira
(74) *Attorney, Agent, or Firm* — Wood IP LLC

(57) ABSTRACT

The present invention relates to a process for purification of iodinated X-ray contrast agents and in particular to purification of crude dimeric contrast agents, such as Iodixanol and Ioforminol. More particularly, the invention relates to purification of such X-ray contrast agents using membrane technology to remove monomeric impurities.

20 Claims, 1 Drawing Sheet

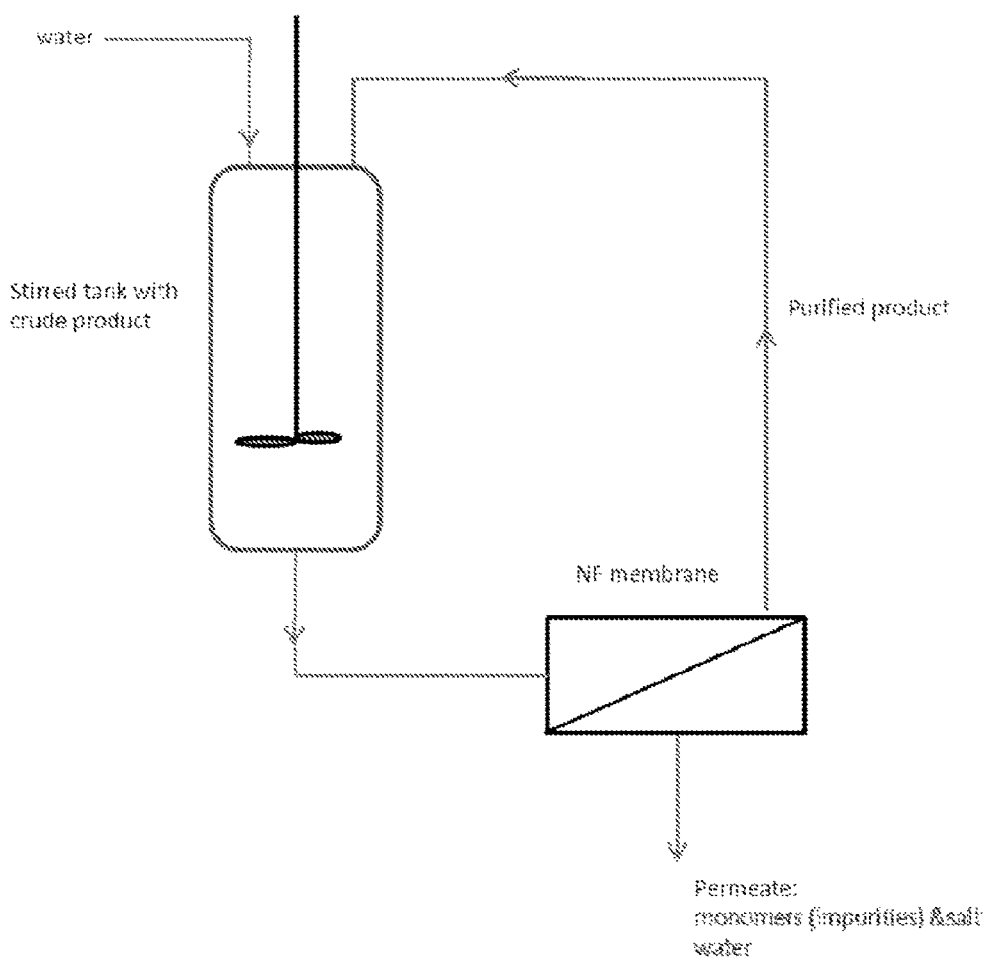

PURIFICATION OF X-RAY CONTRAST AGENTS

This application is a filing under 35 U.S.C. 371 of international application number PCT/US2013/070699, filed Nov. 19, 2013, which claims priority to European application number 12198020.5, filed Dec. 19, 2012, the entire disclosures of each of which are hereby incorporated by reference.

FIELD OF THE INVENTION

The present invention relates to a process for purification of iodinated X-ray contrast agents and in particular to purification of crude dimeric contrast agents, such as Iodixanol and Ioforminol.

BACKGROUND OF THE INVENTION

X-ray contrast media containing a chemical compound as the active pharmaceutical ingredient(s) having two triiodinated phenyl groups linked by a linking group are usually referred to as dimeric contrast agents or dimers. During the years a wide variety of iodinated dimers have been proposed. Currently, one contrast medium having an iodinated non-ionic dimer as the active pharmaceutical ingredient is on the market, the product Visipaque™ containing the compound (contrast agent) Iodixanol.

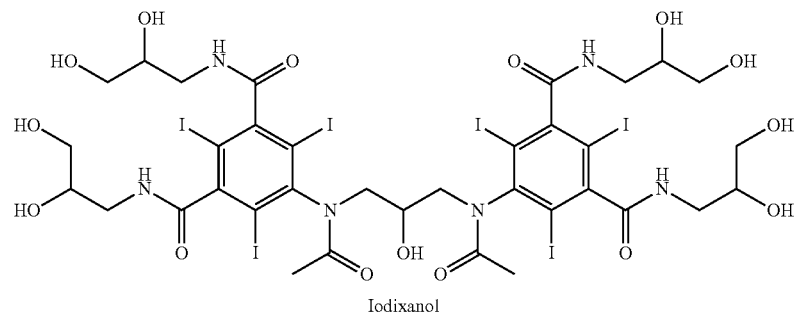 [SMILES: CC(=O)N(CC(O)CN(C(C)=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

Iodixanol

In WO2009/008734 of the applicant a novel dimeric contrast agent named Ioforminol is disclosed. The properties of this is described in more detail in the publications Chai et al. "Predicting cardiotoxicity propensity of the novel iodinated contrast medium GE-145: ventricular fibrillation during left coronary arteriography in pigs", Acta Radiol, 2010, and in Wistrand, L. G., et al "GE-145, a new low-osmolar dimeric radiographic contrast medium", Acta Radiol, 2010. Ioforminol (GE-145) is named Compound 1 herein and has the following structure:

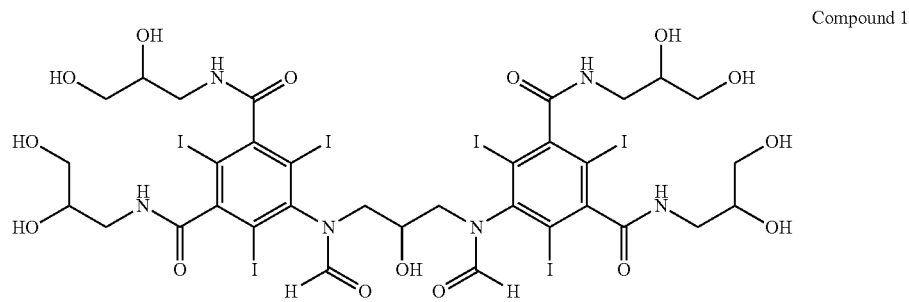 [SMILES: O=CN(CC(O)CN(C=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

Compound 1

5,5'-(2-Hydroxypropane-1,3-diyl)bis(formylazanediyl)bis(N$^1$,N$^3$-bis(2,3-dihydroxypropyl)-2,4,6-triiodoisophthalamide).

The manufacture of non-ionic X-ray contrast media involves the production of the chemical drug, the active pharmaceutical ingredient (API), i.e. the contrast agent, followed by the formulation into the drug product, herein denoted the X-ray composition or contrast media.

WO2006/016815 of the applicant provides an overview of possible synthetic routes to prepare Iodixanol. As shown in scheme I of this Iodixanol can be prepared from, or via, 5-amino-N,N'-bis-(2,3-dihydroxy-propyl)-2,4,6-triiodo-isophthalamide (Compound B), which is commercially available. The free amino group of this is then acylated to provide an acetyl group and the hydroxyl groups in the substituents may also be protected by acylation. In at last step the final intermediate 5-acetamido-N,N'-bis(2,3-dihydroxypropyl)-2,4,6-triiodo-isophthalamide (also called "Compound A") is reacted with a bis-alkylation agent such as epichlorohydrin to yield the dimeric contrast agent Iodixanol. Similarly, WO2009/008734 of the applicant provides a synthetic route for preparing the contrast agent Ioforminol. This agent may also be synthesized from 5-amino-N,N'-bis-(2,3-dihydroxy-propyl)-2,4,6-triiodo-isophthalamide (Compound B). The free amino group of the isophthalamide compound is then acylated to provide a formyl group and the hydroxyl groups in the substituents may also be protected by acylation. The protecting groups may be removed for example by hydrolysis to give N$^1$,N$^3$-bis(2,3-dihydroxypropyl)-5-formylamino-2,4,6-triiodo-isophthalamide and this is reacted with a bis-alkylation agent such as epichlorohydrin to yield the dimeric contrast agent Ioforminol.

Following completion of the synthetic steps preparing a dimeric contrast agent as described above, the crude product comprising the contrast agent needs purification to provide acceptable drug product purity. For a commercial drug product, it is important for the primary production to be efficient and economical and to provide a drug substance fulfilling the regulatory specifications, such as those mandated by the US Pharmacopeia. In addition, the cost of the secondary production depends on the cost of the primary production of the contrast agent, which is directly linked to the efficiency of the synthesis and purification processes in the primary production.

It is therefore critical to optimize each process in the primary production of the contrast agent. For both compounds, Ioforminol and Iodixanol, the best identified synthetic routes involve going from a monomeric molecule to the dimeric molecule in the last step of the syntheses, and it has been identified that the main impurities in the crude products are monomeric compounds and salts. Particularly for Ioforminol the crude Ioforminol product from the syntheses include about 2-10% monomeric impurities, which need to be removed.

The purity of the crude iodixanol product is typically 75-90%, such as only 83-84%, which means that the purification effect needs to be very good to yield a product within the quality requirements. At the same time iodixanol is produced in large quantities, so the yield in the process is very important in terms of financial performance.

Several methods have been described to purify crude products, such as crude X-ray products. U.S. Pat. No. 5,811,581 provides a process for purifying contrast agents using a chromatographic column. The use of liquid chromatography is a disadvantage in industrial processes in particular due to the high costs involved. A more feasible purification method has been found to be crystallization, such as e.g. described in WO2006/016815. However, there are challenges with purifications by crystallization also, such as the long time and the large volume equipment needed, and a disadvantage is especially the loss of yield during the process involving incomplete precipitation before filtration and washing. Crystallizations also have the drawback of high energy consumption as they will typically include reflux of organic solvents and recovery of such. US2001/0021828 of the applicant relates to Iodixanol and to a method of recovering intermediate 5-acetamido-N,N-bis(2,3-dihydroxypropyl)-2,4,6-triiodoisophthalamide (Compound A) from the desalinated and desolventized dimerisation reaction mixture. That invention comprises a method using ultrafiltration prior to the crystallisation of Iodixanol to recover non-crystalline Compound A. U.S. Pat. No. 5,221,485 discloses the use of nano filtration as an alternative or substitute method for the purification of a crude diagnostic agent, such as an X-ray contrast agent. Particularly, a method of purifying crude Ioversol, a monomeric compound, by removing small molecular weight process impurities such as ethylene glycol and dimethylsulfoxide using reverse osmosis is disclosed. The problem to be solved by the present invention may be regarded as the provision of an alternative purification procedure for crude dimeric X-ray contrast agents, avoiding chromatography and crystallization, and wherein monomeric impurities are removed.

SUMMARY OF THE INVENTION

A process has been sought wherein the crude dimeric contrast agent is purified providing a high yield, wherein crystallisation of crystals is avoided, which is easy to scale up and which provides a purified agent in short time. A process has now been identified using membrane technology to remove monomeric compound impurities and salts from the crude product of dimeric X-ray contrast agents.

Accordingly, in a first aspect the invention provides a process for the purification of a crude dimeric X-ray contrast agent product comprising the step of i) passing a solution of the crude product across a membrane (M1) such that monomeric compound impurities and salts cross the membrane (permeate, P1) and the dimeric X-ray contrast agent passes over the membrane (retentate, R1) providing a purified dimeric X-ray contrast agent.

BRIEF DESCRIPTION OF THE DRAWINGS

FIG. 1 shows the process of the first aspect wherein a crude product is purified by separating purified product from monomeric impurities and salts.

DETAILED DESCRIPTION OF THE PREFERRED EMBODIMENTS

Surprisingly it has been found possible to provide an industrially viable process, useful also in large scale, wherein both monomeric impurities and salts are separated from the dimeric contrast agent by using membrane separation.

The crude dimeric X-ray contrast agent product to be purified by the process of the invention is the product obtained from the syntheses, in a raw non-purified state. This crude product is preferably in the form of a solution, wherein the solvent comprises the solvent used in the last step of the synthetic route. The solvent is e.g. water or an alcohol or mixtures thereof, and this may comprise water, 2-methoxyethanol, methanol, propylene glycol, propanol and 1-methoxy-propanol. The crude product comprises the prepared dimeric X-ray contrast agent as the main component and this should be present in an amount of generally at least 60%. For Iodixanol the crude product typically comprises 75-90 weight % Iodixanol. In addition the crude product comprises monomeric impurities, typically 3-10 weight % Iohexol and 0-7 weight % Compound A for Iodixanol. For Ioforminol the crude product typically comprises 75-90 weight % Ioforminol and 1-25 weight %, such as 2-10 weight %, monomeric impurities.

The dimeric X-ray contrast agent is a compound comprising two triiodinated aryl groups linked by a linking group, and in particular, compounds comprising aryl groups with iodine atoms in the 1, 3 and 5 positions are preferred, i.e. such as elements derived from 5-amino-isophtalic acid. These compounds form the class of compounds denoted non-ionic iodinated dimeric X-ray contrast compounds or agents. The molecular weight of the dimeric contrast agent varies dependent on which substituents are included, but this would generally be around 1400-1700 Da. The molecular weight of Iodixanol is 1550 Da and the molecular weight of Ioforminol is 1522 Da. In one embodiment, the dimeric X-ray contrast agent is a compound of formula (I)

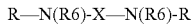   Formula (I)

wherein
X denotes a C3 to C8 straight or branched alkylene moiety optionally with one or two CH$_2$ moieties replaced by oxygen atoms, sulphur atoms or NR4 groups and wherein the alkylene moiety optionally is substituted by up to six —OR4 groups;
R4 denotes a hydrogen atom or a C1 to C4 straight or branched alkyl group;
R6 denotes a hydrogen atom or an acyl function; and
each R independently is the same or different and denotes a triiodinated phenyl group, preferably a 2,4,6-triiodinated phenyl group, further substituted by two groups R5 wherein each R5 is the same or different and denotes a hydrogen atom or a non-ionic hydrophilic moiety, provided that at least one R5 group in the compound of formula (I) is a hydrophilic moiety.

X preferably denotes a straight C3 to C8 alkylene chain optionally substituted by one to six —OR4 groups. More preferably X denotes a straight C3 to C5 alkylene chain having at least one —OR4 group, preferably with at least one hydroxyl group in a position that is not vicinal to the bridge nitrogen atom. More preferably the alkylene chain is substituted by one to three hydroxyl groups and still more preferably the alkylene chain is a straight propylene, butylene or pentylene chain substituted by one, two or three hydroxyl groups. Particularly preferred groups X are selected from 2-hydroxy propylene, 2,3-dihydroxy butylene, 2,4-dihydroxy pentylene and 2,3,4-trihydroxy pentylene, and most particularly X is the 2-hydroxy propylene entity.

R4 preferably denotes a hydrogen atom or a methyl group, most preferably a hydrogen atom. The R6 substituents may be the same or different and preferably R6 denotes a hydrogen atom or a residue of an aliphatic organic acid, and in particular a C1 to C5 organic acid such as formyl, acetyl, propionyl, butyryl, isobutyryl and valeriyl moieties. Hydroxylated and metoxylated acyl moieties are also feasible. In a particularly preferred embodiment the R6 groups individually denote a formyl moiety or acetyl moiety.

Each of the iodinated R groups can be the same or different and preferably denote a 2,4,6-triiodinated phenyl group, further substituted by two groups R5 in the remaining 3 and 5 positions in the phenyl moiety. The non-ionic hydrophilic moieties, R5, may be any of the non-ionizing groups conventionally used to enhance water solubility. Hence, the R5 substituents may be the same or different and shall preferably all denote a non-ionic hydrophilic moiety comprising esters, amides and amine moieties, optionally further substituted by a straight chain or branched chain C1-10 alkyl groups, preferably C1-5 alkyl groups, where the alkyl groups also may have one or more CH2 or CH moieties replaced by oxygen or nitrogen atoms. The R5 substituents may also further contain one or more groups selected from oxo, hydroxyl, amino or carboxyl derivative, and oxo substituted sulphur and phosphorus atoms. Each of the straight or branched alkyl groups preferably contains 1 to 6 hydroxy groups and more preferably 1 to 3 hydroxy groups. Therefore, in a further preferred aspect, the R5 substituents are the same or different and are polyhydroxy C1-5 alkyl, hydroxyalkoxyalkyl with 1 to 5 carbon atoms and hydroxypolyalkoxyalkyl with 1 to 5 carbon atoms, and are attached to the iodinated phenyl group via an amide or a carbamoyl linkage, preferably amide linkages.

The R5 groups of the formulas listed below are particularly preferred:
—CONH$_2$
—CONHCH$_3$
—CONH—CH$_2$—CH$_2$—OH
—CONH—CH$_2$—CH$_2$—OCH$_3$
—CONH—CH$_2$—CHOH—CH$_2$—OH
—CONN—CH$_2$—CHOCH$_3$—CH$_2$—OH
—CONH—CH$_2$—CHOH—CH2-OCH3
—CON(CH$_3$)CH$_2$—CHOH—CH$_2$OH
—CONH—CH—(CH$_2$—OH)$_2$
—CON—(CH$_2$—CH$_2$—OH)$_2$
—CON—(CH$_2$—CHOH—CH$_2$—OH)$_2$
—CONH—OCH$_3$
—CON (CH$_2$—CHOH—CH$_2$—OH) (CH$_2$—CH$_2$—OH)
—CONH—C(CH$_2$—OH)$_2$CH$_3$,
—CONH—C(CH$_2$—OH)$_3$, and
—CONH—CH (CH2-OH) (CHOH—CH2-OH)
—NH(COCH$_3$)
—N(COCH$_3$) C1-3 alkyl
—N(COCH$_3$)— mono, bis or tris-hydroxy C1-4 alkyl
—N(COCH$_2$OH)—hydrogen, mono, bis or tris-hydroxy C1-4 alkyl
N(CO—CHOH—CH$_2$OH)— hydrogen, mono, bis or trihydroxylated C1-4 alkyl.
—N(CO—CHOH—CHOH—CH$_2$OH)— hydrogen, mono, bis or trihydroxylated C1-4 alkyl
—N(CO—CH—(CH$_2$OH)$_2$)— hydrogen, mono, bis or trihydroxylated C1-4 alkyl; and
—N(COCH$_2$OH)$_2$ Even more preferably the R5 groups will be equal or different and denote one or more moieties of the formulas —CONN—CH$_2$—CH$_2$—OH, —CONN—CH$_2$—CHOH—CH$_2$—OH, —CON(CH$_3$)CH$_2$—CHOH—CH$_2$OH, —CONH—CH—(CH$_2$—OH)$_2$ and —CON—(CH$_2$—CH$_2$—OH)$_2$. Still more preferably both R groups are the same and the R2 groups in each R are the same or different and denote —CONN—CH$_2$—CH$_2$—OH, —CONH—CH$_2$—CHOH—CH$_2$—OH, CON(CH$_3$)CH2-CHOH—

CH2OH, —CON—(CH$_2$—CH2-OH)$_2$ and —CONH—CH—(CH$_2$—OH)$_2$. In a particularly preferred embodiment, both R groups are the same and all R5 groups denote the entity of formula —CONN—CH$_2$—CHOH—CH$_2$—OH.

Most preferably the dimeric X-ray contrast agent is Iodixanol or Ioforminol and most preferably it is Ioforminol.

The monomeric compound impurities being removed by the process of the invention are compounds comprising only one aryl group, in particular compounds comprising one aryl group with iodine atoms in the 2, 4 and 6 position. The monomeric compounds have molecular weight less than 900 Da, such as between 435 and 900 Da, more often of 650-900 Da, such as 700-850 Da. The monomeric compound impurities are unreacted starting materials, intermediates from the syntheses of the dimeric X-ray contrast agent, or may be bi-products from these. When the dimeric X-ray contrast agent is Ioforminol the main impurities comprise the following monomeric compounds:

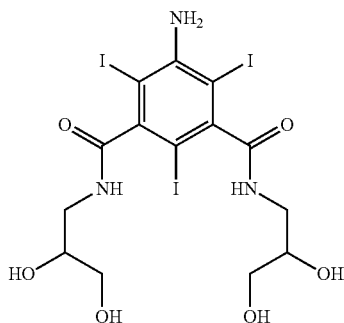 [SMILES: Nc1c(I)c(C(=O)NCC(O)CO)c(I)c(C(=O)NCC(O)CO)c1I]

5-Amino-N1,N3-bis(2,3-dihydroxypropyl)-2,4,6-triiodo-isophthalamide (Compound B);

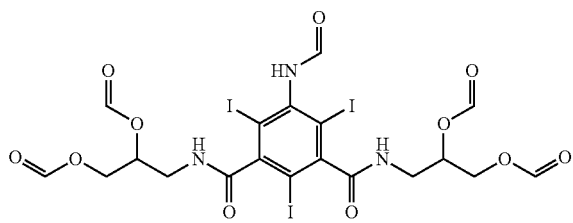 [SMILES: O=CNc1c(I)c(C(=O)NCC(COC=O)OC=O)c(I)c(C(=O)NCC(COC=O)OC=O)c1I]

1-Formylamino-3,5-bis(2,3-bis(formyloxy)propan-1-ylcarbamoyl)-2,4,6-triiodobenzene;

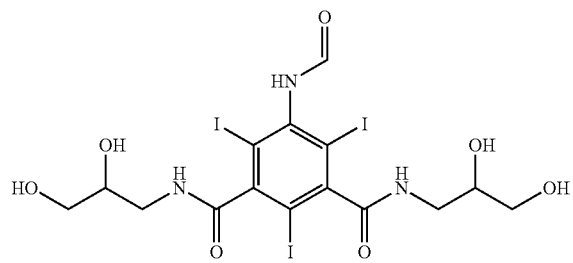 [SMILES: O=CNc1c(I)c(C(=O)NCC(O)CO)c(I)c(C(=O)NCC(O)CO)c1I]

N$^1$,N$^3$-Bis(2,3-dihydroxypropyl)-5-formylamino-2,4,6-thiodoisophthalamide (Compound C).

When the dimeric X-ray contrast agent is Iodixanol the main impurities comprise the following monomeric compounds:

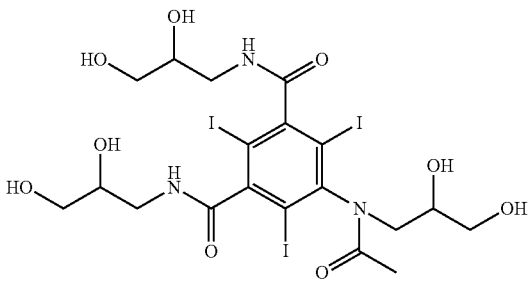 [SMILES: CC(=O)N(CC(O)CO)c1c(I)c(C(=O)NCC(O)CO)c(I)c(C(=O)NCC(O)CO)c1I]

Iohexol;

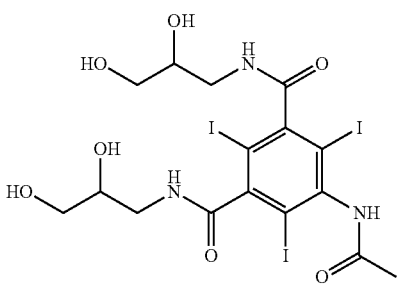 [SMILES: CC(=O)Nc1c(I)c(C(=O)NCC(O)CO)c(I)c(C(=O)NCC(O)CO)c1I]

5-acetamido-N,N'-bis(2,3-dihydroxypropyl)-2,4,6-thiodo-isophthalamide (Compound A);

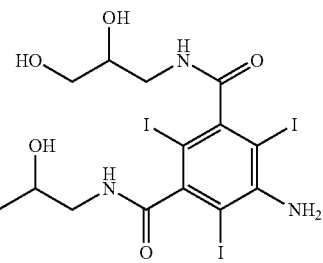

5-amino-N,N'-bis(2,3-dihydroxypropyl)-2,4,6-triiodo-isophthalamide (Compound B).

The crude dimeric X-ray contrast agent product obtained from the synthesis also contains a considerable amount of salts. For Ioforminol and Iodixanol the main salt formed during the syntheses is sodium chloride (NaCl). The sources of chloride are e.g. epichlorohydrin, which may be used in the last bis-alkylation step for both the preparation of Iodixanol and Ioforminol, and hydrochloric acid, which is used to adjust the pH before epichlorohydrin addition and to precipitate unreacted material after the reaction. The source of sodium cations is the sodium hydroxide used to dissolve intermediates in the reaction solvent. Any salts in the crude contrast agent product may be removed by the process of the invention. Other salts that may be removed by the process of the invention are e.g. sodium formiate and sodium acetate. The choice of reagents, acids and bases used in the synthesis of the contrast agent will of course affect which salts are generated.

It has now been found that the process of the invention simultaneously reduces the salt content and the content of monomeric impurities to the desired levels in a cost-effective manner. Only a minimal amount of the dimeric contrast agent is lost during the instant process, hence the process provides the contrast agent in a high yield of high purity in a cost-efficient manner. The retentate (R1) of the step (i) of the process of the invention is retained and collected and comprises the purified dimeric X-ray contrast agent. The single step of the process provides an acceptable drug product purity level of the dimeric agent. This will typically hold a purity of at least 98.0%, preferably at least 98.5%, and most preferably at least 99.0%.

In one embodiment the solution of the crude product passes the membrane (M1) in several cycles to achieve necessary purity, alternatively a series of membranes may be used to reduce the number of cycle times. Hence, the purified product, the retentate R1, from step (i) may be returned to the tank comprising the crude product and mixed with this to perform another cycle. After a certain number of cycles the purified dimeric X-ray contrast agent can be tapped, e.g. from the tank that initially comprised the crude product. As the purified contrast agent is in solution, as a purified retentate, this can simply be precipitated and evaporated, optionally after up-concentrating this, or this may be kept and delivered as liquid bulk. When using the process of the invention there is no need for crystallisation, filtration and washing of crystals. Further, no additional organic solvents are used in the process, hence the use of organic solvents in the purification step is eliminated compared to other methods for purifying crude X-ray contrast agent products, providing an environmentally friendly process. Additional benefits are that the process has low energy consumption, as this is limited to circulation and pressure generation, that it has a short processing time and that it is easy to scale up. Considerable processing time is saved compared to purification including crystallisation.

The monomeric impurities and the salts are separated from the dimeric contrast agent compound by using a membrane separation. The material of the membrane to be used is polymeric or ceramic, and various materials may be used in such. The membrane (M1) has a cut-off size, i.e. a pore size, between 950 and 1200 Da, more preferably between 1000 and 1100 Da and most preferably around 1000 Da. The membrane with this characteristic will reject organic species with a nominal molecular weight of 1000 Da or greater. Therefore the monomeric impurities, with a molecular weight of typically 650-900 Da, and the smaller salts, will be removed from the dimeric compound, as they will cross the membrane (M1, P1). As no membrane has perfectly uniform pores, and since chemical compounds, such as dimeric compounds, can have different conformations, some dimeric contrast agent compound will however cross the membrane alongside the monomeric impurities. Hence, some dimeric compound may be lost during this main step of the process separating monomers from dimers. An example of a useful membrane is Hydranautics 50, 1 KDa, but there are alternative equivalent membranes available such as from Pall membrane and from Inopor.

In one embodiment of the invention the process comprises a second step ii) to separate salts from the monomeric impurities. In this embodiment the permeate from step i) (P1) comprising monomeric impurities and salts is passed across another membrane (M2) such that salts cross the membrane (permeate, P2) and the monomeric compound impurities passes over the membrane (retentate, R2), and wherein the retentate R2 is retained. In this embodiment the salts are separated from the monomeric impurities, and the solution of monomers is preferably up-concentrated. The retentate (R2) from step ii) comprises monomeric compound impurities and may also comprise a minor part of the dimeric contrast agent that leaked through the membrane (M1) in the first step.

To achieve a high overall yield of the dimeric contrast agent any dimeric compound in the permeate (P1) or the retentate (R2), if step ii) has been performed, should be recovered. In a further embodiment of the invention the permeate (P1) from step i) comprising mainly monomeric impurities, or the retentate (R2) from step (ii) comprising up-concentrated monomeric impurities, and which have had salts removed, are subject to another round of purification by performing step (i) of the process again. In a preferred embodiment, the retentate (R2) comprising mainly monomeric impurities is transferred back to the crude product and mixed with this, or is combined with a feed stream from the crude product and hence mixed with this, such that the next batch of crude product to be purified includes any dimeric contrast agent that was lost in the previous batch, and then step i) is repeated.

The membrane (M2) used in the second step of separating salts from monomeric impurities has a cut-off size between 80 and 400 Da, more preferably between 100 and 300 Da. The membrane with this characteristic will reject organic species with a nominal molecular weight of 400 Da or greater. The membrane M2 is preferably a nanofiltration membrane used for salt removal. Therefore the salts, with a molecular weight of typically 50-80 Da, will easily cross the membrane and be removed from the monomeric impurities and any remaining dimeric x-ray contrast agent. The permeate (P2) from the second step of the process comprises salts, and hence impurities of low molecular weight. This diluted salt solution may go to waste. Alternatively, a third membrane system with a reverse osmosis membrane could be used to recover water for recycling and reuse.

The monomeric impurities from the retentate R2 of the second step, or alternatively after any remaining minor part of the dimeric product has been removed and retained, may be used either for recovery of iodine or may be used in synthesis of X-ray contrast agent, optionally after purification.

The equipment used in the process of the invention comprises a membrane system comprising at least a tank for delivery of the crude dimeric X-ray contrast agent product, a pump for feeding a feed stream of the crude product, and a membrane (M1), coupled together. In addition piping and valves are present.

Process parameters like feed stream flow, pressure and temperature may affect the volume and time efficiency and the selectivity of the purification. The flow of the feed stream of the dimeric X-ray contrast agent to be purified may typically be in the range of 5-15 litre/hour/m$^2$ and the temperature used in the process is e.g. 10-35° C. With a moderate flow a good volume and time efficiency is obtained, but if increasing the pressure and hence the flow the selectivity of the purification, between monomers and dimers, is improved.

The purified X-ray contrast agents according to the invention may be used as contrast agents and may be formulated with conventional carriers and excipients to produce diagnostic contrast media. Thus viewed from a further aspect the invention provides a diagnostic composition comprising a dimeric contrast agent, preferably Ioforminol or Iodixanol, purified according to the process of the invention, together with at least one physiologically tolerable carrier or excipient, e.g. in aqueous solution for injection optionally together with added plasma ions or dissolved oxygen. The contrast agent composition of the invention may be in a ready to use concentration or may be a concentrate form for dilution prior to administration. Hence, the invention further embraces use of the contrast agent purified according to the process of the invention, and a diagnostic composition containing such, in X-ray contrast examinations.

In a still further aspect the invention provides Iodixanol or Ioforminol as obtained by the process of the invention and where the obtained product is of a purity fulfilling the required drug product purity, such as those e.g. given by the specification of the US Pharmacopea.

The invention is illustrated with reference to the following non-limiting examples.

EXAMPLES

Example 1

Purification of a Crude Ioforminol Solution by Membrane Technology

A solution of a crude product comprising 93.8% Ioforminol, 3% monomeric impurities, 3% salts and 0.2% trimeric impurities in a stirred tank was feed into a membrane system comprising a Hydranautics 50, 1 KDa membrane to separate monomeric impurities and salts from the dimeric compound Ioforminol.

Results:

Analysing the first retentate, this consisted of 99.27% Ioforminol and only 0.05% 1-Formylamino-3,5-bis(2,3-bis(formyloxy)propan-1-ylcarbamoyl)-2,4,6-triiodobenzene (Compound B),
0.14% $N^1,N^3$-Bis(2,3-dihydroxypropyl)-5-formylamino-2,4,6-thiodoisophthalamide (Compound C) and some other impurities, totally 0.73% impurities.

The invention claimed is:

1. A process of purifying a crude dimeric X-ray contrast agent product that comprises monomeric compound impurities and salts and a dimeric agent that is the dimer of the monomeric compound, the process comprising a first step of
i) passing a solution of the crude product across a membrane (M1) such that the monomeric compound impurities and the salts cross the membrane (permeate, P1) and the dimeric X-ray contrast agent passes over the membrane (retentate, R1), to provide a purified dimeric X-ray contrast agent,
wherein the monomeric compound impurities are compounds having a molecular weight between 435 and 900 Da, and
wherein M1 has a cut-off size between 950 and 1200 Da.

2. The process of claim 1, wherein the dimeric X-ray contrast agent has a molecular weight of 1400-1700 Da.

3. The process of claim 1, wherein the dimeric X-ray contrast agent is Ioforminol or Iodixanol.

4. The process of claim 1, wherein the monomeric compound impurities have a molecular weight between 700 and 850 Da.

5. The process of claim 1, wherein the retentate (R1) of the step (i) is retained and collected.

6. The process of claim 1, wherein the purified dimeric X-ray contrast agent obtained holds a purity of at least 98%.

7. The process of claim 1, wherein there is less than 2% of the monomeric compound impurities and salts left in R1 after the process is conducted.

8. The process of claim 1, further comprising a second step
ii) wherein the permeate from step i) (P1) is passed across another membrane (M2) such that salts cross this membrane (permeate, P2) and the monomeric compound impurities passes over the membrane (retentate, R2), and wherein the retentate R2 is retained.

9. The process of claim 8, wherein the permeate (P1) from step i), or the retentate (R2) from step (ii), is subject to another round of purification by repeating step (i) of the process to recover dimeric X-ray contrast agent lost in the first round.

10. The process of claim 8, wherein the retentate R2 is transferred to the crude product and mixed with this crude product, or is combined with a feed stream from the crude product, before repeating step i).

11. A composition comprising a dimeric contrast agent purified according to the process as claimed in claim 1, together with at least one physiologically tolerable carrier or excipient.

12. A process of purifying a crude dimeric X-ray contrast agent product that comprises monomeric compound impurities and salts and a dimeric agent that is the dimer of the monomeric compound, the process comprising a first step of
i) passing a solution of the crude product across a membrane (M1) such that the monomeric compound impurities and the salts cross the membrane (permeate, P1) and the dimeric X-ray contrast agent passes over the membrane (retentate, R1),
wherein the retentate (R1) of the step (i) is retained and collected to provide a purified dimeric X-ray contrast agent, and wherein the dimeric X-ray contrast agent has a molecular weight of 1400-1700 Da, and
wherein there is less than 2% of the monomeric compound impurities and salts left in R1 after the process is conducted, and
wherein M1 has a cut-off size between 950 and 1200 Da.

13. The process of claim 12, wherein the dimeric X-ray contrast agent is Ioforminol or Iodixanol.

14. The process of clam 12, wherein the purified dimeric X-ray contrast agent obtained holds a purity of at least 98%.

15. The process of claim 12, wherein a membrane (M1) is used having a cut-off size between 950 and 1200 Da.

16. The process of claim 12, further comprising a second step
ii) wherein the permeate from step i) (P1) is passed across another membrane (M2) such that salts cross this membrane (permeate, P2) and the monomeric compound impurities passes over the membrane (retentate, R2), and wherein the retentate R2 is retained.

17. The process of claim 16, wherein the permeate (P1) from step i), or the retentate (R2) from step (ii), is subject to another round of purification by repeating step (i) of the process to recover dimeric X-ray contrast agent lost in the first round.

18. The process of claim 16, wherein the retentate R2 is transferred to the crude product and mixed with this crude product, or is combined with a feed stream from the crude product, before repeating step i).

19. A composition comprising a dimeric contrast agent purified according to the process as claimed in claim 12, together with at least one physiologically tolerable carrier or excipient.

20. The process of clam 12, wherein the purified dimeric X-ray contrast agent obtained holds a purity of at least 99.0%.

* * * * *